(12) United States Patent
Beez et al.

(10) Patent No.: US 9,808,954 B2
(45) Date of Patent: Nov. 7, 2017

(54) COMPOSITION OF A TIMBER FORMULATION COMPRISING CU SALTS AND ORGANIC CYCLIC INGREDIENTS FOR THE PRESERVATION OF TIMBER FOR DECKS

(71) Applicant: Rutgers Organics GmbH, Mannheim (DE)

(72) Inventors: Volker Beez, Bürstadt (DE); Helmut Härtner, Dirmstein (DE); Stefan Schmitt, Birkenau/Reisen (DE)

(73) Assignee: Rutgers Organics GmbH, Mannheim (DE)

( * ) Notice: Subject to any disclaimer, the term of this patent is extended or adjusted under 35 U.S.C. 154(b) by 0 days.

(21) Appl. No.: 14/826,538

(22) Filed: Aug. 14, 2015

(65) Prior Publication Data

US 2016/0046036 A1 Feb. 18, 2016

Related U.S. Application Data

(60) Provisional application No. 62/038,020, filed on Aug. 15, 2014.

(51) Int. Cl.
*B27K 3/22* (2006.01)
*A01N 59/20* (2006.01)
*A01N 43/653* (2006.01)
*A01N 55/08* (2006.01)
*C09D 5/14* (2006.01)

(52) U.S. Cl.
CPC ............. *B27K 3/22* (2013.01); *A01N 43/653* (2013.01); *A01N 55/08* (2013.01); *A01N 59/20* (2013.01); *C09D 5/14* (2013.01)

(58) Field of Classification Search
CPC ........ B27K 3/22; A01N 43/653; A01N 55/08; A01N 59/20; C09D 5/14
USPC ........................................................ 428/541
See application file for complete search history.

(56) References Cited

U.S. PATENT DOCUMENTS

| | | | | |
|---|---|---|---|---|
| 4,801,404 A * | 1/1989 | Dietrich | ................ | B27K 3/12 106/18.13 |
| 4,970,201 A | 11/1990 | Giebeler et al. | | |
| 5,078,912 A | 1/1992 | Goettsche et al. | | |
| 5,304,237 A | 4/1994 | Barth et al. | | |
| 5,714,507 A | 2/1998 | Valcke et al. | | |
| 5,916,356 A | 6/1999 | Williams et al. | | |
| 6,274,199 B1 * | 8/2001 | Preston | ................ | B27K 3/0207 427/297 |
| 6,506,795 B1 | 1/2003 | Barth et al. | | |
| 7,264,886 B2 * | 9/2007 | Cui | ..................... | C09D 191/06 427/294 |
| 7,674,481 B2 | 3/2010 | Leach et al. | | |
| 7,850,771 B2 * | 12/2010 | Cui | ........................ | A01N 25/02 106/15.05 |
| 7,896,960 B2 * | 3/2011 | Ward | ..................... | A01N 33/12 106/15.05 |
| 7,993,756 B2 * | 8/2011 | Jin | ........................ | B27K 3/16 427/298 |
| 8,168,304 B2 * | 5/2012 | Zhang | .................... | B27K 3/005 106/18.13 |
| 8,293,282 B2 | 10/2012 | Patel | | |
| 8,747,909 B2 * | 6/2014 | Leach | .................... | A01N 25/04 424/630 |
| 2002/0083864 A1 | 7/2002 | Higaki | | |
| 2009/0158961 A1 | 6/2009 | Zhang et al. | | |

FOREIGN PATENT DOCUMENTS

| | | |
|---|---|---|
| AU | 2007203237 A1 | 2/2008 |
| CN | 1633853 | 7/2005 |
| DE | 3447027 A1 | 7/1986 |
| DE | 3502939 A1 | 7/1986 |
| DE | 3621360 A1 | 1/1988 |
| DE | 3718012 A1 | 12/1988 |
| DE | 4228352 A1 | 8/1993 |
| DE | 4339701 A1 | 5/1995 |
| DE | 19524286 A1 | 1/1997 |
| EP | 0355316 A2 | 2/1990 |
| EP | 0498162 A1 | 8/1992 |
| EP | 554883 A2 | 8/1993 |
| EP | 0556454 A1 | 8/1993 |
| JP | 2003272705 A | 9/2003 |
| WO | WO-9002557 A1 | 3/1990 |

(Continued)

OTHER PUBLICATIONS

"Magazine for the processing of chemical feedstocks, industrial auxiliaries, solvents-wax and resin processing", Seifen-Ole-Fette-Wachse 109(20), 1983, pp. 603-606.
Impralit. Techn. Merkblatt Holzschutzsysteme Impralit-KDS 4; Für die Kesseldruck-Imprägnierung Gebrauschsklassen pp. 1-4.
Cui et al., "What to Look for in a Wood Preservative?" Rütgers Organics.
Cui et al., "Polymeric Betaine as a Wood Preservative," The International Research Group on Wood Protection, 2008, pp. 1-11.
Härtner et al., "Impralit KDS and KDS-B," Proceedings, American Wood Protection Association, 2009, pp. 128-135.
Härtner et al., "The Chemical and Biological Properties of Polymeric Betaine," The International Research Group on Wood Protection, 2009, pp. 1-8.
Schmitt et al., "Copper-Based Wood Preservative Systems Used for Residential Applications in North America and Europe," American Chemical Society, 2014, pp. 218-225.

(Continued)

*Primary Examiner* — Leszek Kiliman
(74) *Attorney, Agent, or Firm* — Blank Rome LLP; Charles R. Wolfe, Jr.

(57) ABSTRACT

This invention relates to a composition, a process for producing a composition, a timber formulation, a process for producing a timber formulation, a construction comprising the timber formulation and a use of the construction comprising the timber formulation are herein disclosed. The composition can include a Cu-salt, a first cyclic organic compound comprising a B heteroatom and at least one further B-free cyclic organic compound. The composition and timber formulation herein disclosed are designed as wood preservatives and may be used as part of a timber preserving treatment.

44 Claims, 4 Drawing Sheets

(56) References Cited

FOREIGN PATENT DOCUMENTS

| WO | WO-9302557 A1 | 2/1993 |
|---|---|---|
| WO | WO-9514558 A1 | 1/1995 |
| WO | WO-0193677 A1 | 12/2001 |
| WO | WO-2004091875 A2 | 10/2004 |
| WO | WO-2007028526 A2 | 3/2007 |
| WO | WO-2009014106 A1 | 1/2009 |
| WO | WO-2011038747 A1 | 4/2011 |

OTHER PUBLICATIONS

Carr et al., "Wood Protection Properties of Quaternary Ammonium Spiroborate Esters Derived for Alkyl Tartrates," Aust. J. Chem., 2001, pp. 495-502.
Carr et al., "Quaternary Ammonium Arylspiroborate Esters as Oragno-Soluble Environmentally Bengin Wood Protectants," Aust. J. Chem., 2005, pp. 901-911.
Barth et al., "A new Type of biocide suitable for use in different fields of wood preservation," The International Research Group on Wood Preservations, 1993, pp. 1-8.
Härtner et al., "Effectiveness and Synergistic effects between Copper and Polymer Betaine," The International Research Group on Wood Preservation, 1996, pp. 1-9.
Safety Data sheet according to 1907/2006/EC, Article 31; Version No. 1, pp. 1-9.
ICC Evaluation Service, "Proposed Revisions to the Acceptance Criteria for Proprietary Wood Preservative Systems•Common Requirements for Treatment Process, . . . ", 2014.
McIntyre et al., "Micronized Copper," Proceedings, American Wood Protection Association.
Lonza Ltd., "Product Information: Bardap-26, The free of Chloride Quat," Mar. 20, 2003.
Deutsche Norm: EN 113 "Wood preservatives." 1996.
Deutsche Norm: EN 599 "Dauerhaftigkeit von Holz und Holzprodukten." 1997.
European Committee for Standardization, "Durability of wood and wood-based products—effectiveness of preventive wood preservatives as determined by biological tests—Part 1: specification according to the use class," 2006, pp. 1-35.
Cen, "Wood preservatives—Determination of toxic values against European *Reticulitermes* species (Laboratory method)," 2004, pp. 4-22.
ICC Evaluation Service: Criteria Development—Criteria posted for Public Comment Jun. 2, 2014,Jun. 2, 2014 (Jun. 2, 2014), pp. 1-1, XP55325080, Registered in waybackmachine Jul. 5, 2014, Retrieved from the Internet: URL:https://web.archive.org/web/20140705051535/http:// [retrieved on Dec. 1, 2016].
Rodney C. De Groot et al., "Using copper-tolerant fungi to biodegrade wood treated with copper-based preservatives", International Biodeterioration & Biodegradation, vol. 44, 1999, pp. 17-27.
Olaf Schmidt "Wood and Tree Fungi—Biology, Damage, Protection, and Use", 2006, p. 152.
Mike H. Freeman et al "A Comprehensive Review of Copper-Based Wood Preservatives—With a focus on new micronized or dispersed copper systems", Forest Products Journal, Nov. 2008, vol. 58, No. 11, pp. 6-27.
Wikipedia "Antrodia", Stand 20.10.2015, https://en.wikipedia.org/wiki/Antrodia.
Wikipedia "Fomitopsis palustris", Stand 201.10.2015, http://en.wikipedia.org/wiki/Fomitopsis_palustris.
Screenshot of Abstract for "Production of copper oxalate by some copper tolerant fungi", Murphy and Levy, in Transac Brit Mycol Soc 81 (1) 1983, pp. 165-168.
Ullmann's Encyclopedia of Industrial Chemistry, 6th Edition, vol. 39, 2003, p. 489.

* cited by examiner

COMPOSITION OF A TIMBER FORMULATION COMPRISING CU SALTS AND ORGANIC CYCLIC INGREDIENTS FOR THE PRESERVATION OF TIMBER FOR DECKS

This application claims benefit of U.S. Provisional Application No. 62/038,020, filed Aug. 15, 2014, the content of which is hereby incorporated by reference.

FIELD OF THE INVENTION

In general, the invention relates to a composition, a process for producing a composition, a timber formulation, and a process to produce said timber formulation, wherein the timber formulation can be used to preserve a timber comprised in the timber formulation, and said timber can be used as a construction material. The composition according to the invention, comprises; a Cu-salt, at least one first cyclic organic compound comprising a B heteroatom in a cycle and at least one further B free cyclic organic compound comprising a heteroatom selected from the group of O, N, S, or P, or a combination of at least two thereof in a cycle.

BACKGROUND OF THE INVENTION

Wood is a versatile material which can be used in various industries. Due to its wide range of applications, it is important to ensure its longevity and/or durability and thus, it must be protected. Research into wood preservation and wood preservatives are documented in the prior art. The aim of improving the resistance of wood to environmental hazards, such as, fungal and insect attack, led to the development of preservatives incorporating additives including but not limited to; chromate compounds, quaternary ammonium compounds and copper.

Works relating to wood preservatives in the prior art include Seifen-Öle-Fette-Wachse 109, vol. no. 20, 1983, pages 603 to 606. This document disclosed the use of quaternary ammonium compounds in water-soluble and solvent-containing wood preservatives. Another document is DE-A Nos. 3,502,939, 3,621,360 or 3,718,012 which further disclosed that by combining quaternary ammonium compounds with other organic or inorganic compounds, an increase in protection by the wood preservative was possible. DE-C-34 47 027 disclosed wood preservatives based on copper, boron, alkanol amines and quaternary ammonium salts. A further document, DE-A-42 28 352 disclosed copper salts, alcohol amines and polymeric quaternary ammonium borates

SUMMARY OF THE INVENTION

The prior art has shown that the use of additives including copper-, boron-compounds, alkanol amines and quaternary ammonium salts in a wood preservative have achieved some success in the protection of wood. Their effectiveness however, remains to be further improved in order to ensure the long-term protection of the timber. A timber treated with a short-lasting wood preservative and constructions built using said timber, can lead to increased maintenance costs, since the short-lasting wood preservative has to be frequently renewed.

When wood is used in buildings, it is normal for several timber pieces to be joined via interfaces occurring at the surfaces of each of the timber pieces being joined. These interfaces cannot be as easily maintained as the exterior of the wood. Usually wooden constructions, in particular, decks, are subjected to various amounts of mechanical stress. A major portion of this stress causes that at least two wooden parts of the construction in the area of the interface move against each other. This quite often causes the surface protection of the wooden pieces, such as lacquer or paint, to peel off or deteriorate otherwise. These portions then become more susceptible to environmental hazards, such as insect and fungal attack or moisture and climate changes. With the surface protection now damaged or even completely removed, the impregnation of the timber becomes particularly important for the longevity of the construction. Further deterioration of surface protection can be caused by the holes for screws which are used to connect the timber interfaces. These holes are often easily penetrated by water and cannot be tightly protected by preservative coatings. It is also possible that deck surfacing is destroyed by shoes. Moreover, should soil and/or foliage material come into contact with the areas of the deck surface where the surface protection has been deteriorated, the exposed timber becomes more susceptible to microbe attack, e.g. soft-rot and mold. For at least these aforementioned reasons, it is important that the preservative is able to strongly impregnate the timber. Furthermore, long term efficacy should be obtained.

The general object of this invention is to provide at least a partial solution to at least one of the problems encountered in the state of the art in relation to a chromium-free wood preservative which can remain effective over a long period of time.

Another object of the invention is to provide a formulation aid which allows formation of a more stable and homogeneous dispersion of copper carbonate particles and does so with a reduced need for further surface active ingredients.

Another object of the invention is to provide a composition for treating and preserving timber which shows a good wood preservation performance with a reduced amount of halogen containing active ingredients.

A further object of this invention is to show that whilst copper is known in the art as being an important active ingredient for wood preservatives, it can be significantly enhanced by the presence of at least two, combined, cyclic organic compounds.

It is furthermore an object of the invention to provide a composition and a formulation, for treating and preserving timber, which show a good wood preservation performance with a reduced amount of copper.

Another object of the invention is to provide a composition that can be used in a timber formulation which is subsequently applied to a timber in order to improve the longevity of the timber and a construction using said timber.

More specifically, it is an object of the invention to provide a composition that can improve the mechanical stability of timber constructions.

Another object of the invention is to improve the long term grip of the surfaces of timber decks when used by man.

A further object of the invention is to provide a composition that can improve the durability of the interfaces of at least two timbers and their subsequent long-term mechanical stability.

It is also an object of the invention to provide an efficient process for producing the improved composition and formulation.

It is another objective of the invention to obtain a homogeneous distribution of the active ingredient(s) throughout the timber and its surface.

DETAILED DESCRIPTION

A contribution to achieving at least one of the above described objects is made by the following embodiments

|1| A composition comprising;
  i. a Cu-salt
  ii. at least one first cyclic organic compound comprising a B heteroatom in a cycle;
  iii. at least one further B free cyclic organic compound comprising a heteroatom selected from the group of O, N, S, or P, or a combination of at least two thereof, preferably O or N and more preferably O and N, in a cycle.

It is preferred for any B free cyclic organic compound that the cycle of this compound is a hetero-cycle. Amongst these hetero cyclic compounds those with N or O or both heteroatoms are preferred and those with two or more N hetero atoms are even more preferred.

|2| The composition according to embodiment |1|, wherein the B heteroatom is negatively charged in the at least one first cyclic organic compound comprising a B heteroatom.

|3| The composition according to any one of the preceding embodiments, wherein the composition comprises preferably at least four different further B free cyclic organic compounds, more preferably at least three different further B free cyclic organic compounds, most preferably at least two different further B free cyclic organic compounds.

|4| The composition according to embodiment |3|, wherein the preferably at least two different further B free cyclic organic compounds differ in at least one of the following structural terms:
  (a) the number of halogen atoms, preferably Cl atoms;
  (b) number of cycles, preferably 3 to 6 membered cycles;
  (c) number of heteroatoms other than halogens, preferably N, P or O;
  wherein it is preferred that the at least two different further B free cyclic organic compounds differ in two of these structural terms, it is further preferred that they differ in all three structural terms.

|5| The composition according to embodiment |1|, wherein the copper is present in the composition in a concentration preferably in a range from 0.02-80 wt.-%, more preferably in a range from 0.05-75 wt.-%, most preferably in a range from 0.1-70 wt.-%, each based on the total weight of the composition.

|6| a) The composition according to embodiments |1|-|5|, wherein at least 60 wt.-%, more preferably at least 70 wt.-% and most preferably at least 90 wt.-%, of the copper present in the composition has a particle size in the range from 1-1000 nm, each based on the total weight of the composition.
  b) The composition according to embodiments |1|-|5|, wherein the copper present in the composition has a particle size distribution in the range from 0.05-3000 nm, more preferably in the range from 0.06-2000 nm, most preferably in the range from 0.08-1000 nm.

|7| The composition according to embodiments |1|-|6|, wherein the copper has a $d_{50}$ value preferably in the range from 0.5-500 nm, more preferably in the range from 0.8-400 nm, most preferably in the range from 1-300 nm.

|8| The composition according to embodiments |1|-|7|, wherein the copper has a $d_{90}$ value preferably in the range from 0.5-2000 nm, more preferably in the range from 0.8-1500 nm, most preferably in the range from 1-1000 nm.

|9| The composition according to embodiments |1|-|8|, wherein the copper has a dm value preferably in the range from 0.08-500 nm, more preferably in the range from 0.09-300 nm, most preferably in the range from 0.1-100 nm.

|10| The composition according to any of embodiments |1|-|9|, wherein the Cu-salt is dispersed in a solvent wherein the solvent is preferably a polar solvent, more preferably a protic solvent, most preferably a polar protic solvent, in order to obtain a liquid phase. Preferred solvents may be selected from the group comprising; ketones, amines, alcohols, carboxylic acids, esters or a combination of at least two thereof wherein water and any monoalcohol amine are the most preferred choices. It is preferred to employ water as the solvent, wherein the composition will be a dispersion. It is preferred to employ monoalcohol amine as the solvent, wherein the composition will be a solution.

|11| The composition according to embodiment |10|, wherein the concentration of solvent lies preferably in a range from 1-60 wt.-%, more preferably in a range from 10-55 wt.-%, most preferably in a range from 35-50 wt.-%, each based on the total weight of the composition.

|12| The composition according to any of embodiments |1|-|11|, wherein the first cyclic organic compound is present in the composition preferably in a range from 0.1-60 wt.-%, more preferably in a range from 1-50 wt.-%, most preferably in a range from 5-40 wt.-%, each based on the total weight of the composition.

|13| The composition according to any of embodiments |1|-|12|, wherein the at least one further cyclic compound is present in the composition preferably in a range from 0.01-70 wt.-%, more preferably in a range from 0.05-30 wt.-%, most preferably in a range from 0.05-3 wt.-%, each based on the total weight of the composition.

|14| The composition according to any of the preceding embodiments wherein the first cyclic organic compound is a betain or its derivative or both.

|15| The composition according to any of the preceding embodiments, wherein the further organic compound is a triazole or its derivative or both.

|16| The composition according to any of the preceding embodiments, wherein the first cyclic organic compound is of the general formula (I);

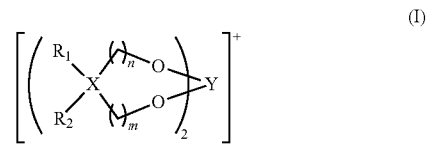

wherein in formula (I)
X is selected from elements; P, N, or B, preferably N;
Y is B;
$R_1$, $R_2$ are independently from each other a saturated linear hydrocarbon containing from 1-20 C atoms, preferably from 5-15 C atoms, more preferably from 8-12 atoms; and
n, m are independently from each other any integer value in the range from 1-20, it is preferred that n is an integer value in the range from 1-20 and m is integer value in the range from 1-20; it is more preferred that n is an integer value in the range from 1-10 and m is integer value in the range from 1-10; it is most preferred that n is an integer value in the range from 2-5 and m is integer value in the range from 2-5.

|17| The composition according to any of the preceding embodiments, wherein the further cyclic organic compound can be of the general formula (II):

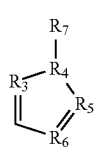

(II)

wherein in formula (II)

$R_3$ is a heteroatom selected from elements C or N, preferably N;

$R_4$ is a non-C heteroatom selected from elements, N, O or S, preferably N or O, most preferably N;

$R_5$ is a heteroatom selected from elements, C, N, O or S, preferably C or N, most preferably C;

$R_6$ is a heteroatom selected from elements C or N, preferably N; and $R_7$ is H, or comprises an organic moiety wherein the organic moiety can comprise at least one heteroatom selected from the group of C, H, O, N, halogen, or a combination of at least two thereof.

In a preferred aspect of the formula (II) $R_3$ is N, $R_4$ is N, $R_5$ is C and $R_6$ is N.

|18| The composition according to any one of the preceding claims, wherein the at least one further B free cyclic organic compound is selected from the group consisting of triadimefon, cyproconazol, tebuconazol, propriconazole or salts of each thereof

|19| The composition according to any of the embodiments |3|-|18| wherein the at least two further B free cyclic organic compounds are preferably tebuconazol and propriconazole or salts of each thereof, wherein tebuconazol and propriconazole are most preferred.

All aspects and embodiments which have been disclosed pertaining to the composition according to the invention, also apply to the corresponding features of the process for producing a composition according to the invention and vice versa.

|20| A further embodiment of this invention is to provide a process for producing a composition, wherein the process comprises at least the following steps;
i. providing a first cyclic organic compound comprising a B heteroatom;
ii. providing at least one further B free cyclic organic compound comprising a heteroatom selected from the group of O, N, S, or P, or a combination of at least two thereof, preferably O or N and more preferably O and N, in a cycle;
iii. providing a Cu-salt;
iv. contacting the first cyclic organic compound comprising a B heteroatom with the at least one further B free cyclic organic compound in a solvent in order to obtain a solution;
v. contacting the solution of step (iv) with a Cu-salt in order to obtain the composition;

|21| The process according to embodiment |20| wherein the Cu-salt is comprised in a liquid phase comprising a solvent wherein the liquid phase can preferably be a solution or a dispersion, wherein a solution is preferred.

|22| The process for producing a composition according to embodiments |20|-|21|, wherein the composition comprises at least two different further B free cyclic organic compounds preferably selected from the group consisting of; triadimefon, cyproconazol, tebuconazol, propriconazole or salts of each thereof. It is preferred that the at least two different further B free cyclic organic compounds are obtained by contacting at least a first and a second B free cyclic organic compound. This contacting is preferably performed prior to the contacting of step iv.

|23| The process for producing a composition according to embodiment |22|, wherein in step iv. the contacting is performed at a temperature preferably in the range from 30-80° C., more preferably in the range from 35-75° C. and most preferably in the range from 40-60° C.

|24| a) The process for producing a composition according to any of embodiments |20|-|23|, wherein the first cyclic organic compound comprising a B heteroatom and the at least one further cyclic organic compound are contacted in a ratio of at least 1:5, wherein 1 is the concentration of the first cyclic organic compound and 5 is the concentration of the at least one further cyclic organic compound, it is more preferred that they are contacted in a ratio of 1:10, with the most preferred ratio being 1:25.

b) The process for producing a composition according to any of embodiments |20|-|23|, wherein the first cyclic organic compound comprising a B heteroatom and the at least one further cyclic organic compound are contacted in a ratio of at least 1:5, wherein 1 is the concentration of the at least one further cyclic organic compound and 5 is the concentration of the first cyclic organic compound, it is more preferred that they are contacted in a ratio of 1:10, with the most preferred ratio being 1:25.

|25| The process for producing a composition according to any of embodiments |20|-|24| wherein the Cu-salt liquid phase, is prepared at a temperature in the range preferably from 5-60° C., more preferably in the range from 10-50° C., most preferably in the range from 15-40° C.

|26| The process for producing a composition according to any of embodiments |20|-|25|, wherein Cu-salt is ground. The Cu-salt can be ground at any stage of the process for preparing the composition according to the invention. It is, however, preferred to grind the Cu-salt in or after step iii. of the process for producing the composition according to the invention. It is more preferred to conduct the grinding in or after step iv. in the process for producing a composition according to the invention.

|27| The process for producing a composition according to embodiment |26|, wherein the Cu-salt is ground until preferably at least 50 wt.-%, more preferably at least 60 wt.-%, most preferably at least 70 wt.-% of the particles are preferably less than 2000 nm in size, more preferably less than 1500 nm in size, most preferably less than 1000 nm in size, based on the total weight of the composition.

|28| The process for producing a composition according to any of embodiments |26| or |27|, wherein the Cu-salt is ground until preferably less than or equal to 30 wt.-%, more preferably less than or equal to 20 wt.-%, most preferably less than or equal to 10 wt.-% of the particles are smaller than 100 nm in size, based on the total weight of the composition.

|29| The process for producing a composition according to any of the embodiments |20|-|28| wherein the composition is a composition according to any one of the embodiments |1|-|19|.

All aspects and embodiments which have been disclosed pertaining to the composition and the process for producing a composition according to the invention, also apply to the corresponding features of both the timber formulation and the process for producing a timber formulation according to the invention and vice versa.

|30| A timber formulation comprising
  a) a composition according to any of the preceding claims; and
  b) a timber;
  wherein the composition is present in the timber.

|31| The timber formulation according to embodiment |30|, wherein the timber comprises sapwood in the range preferably from 10-80%, more preferably from 25-65%, most preferably from 45-55% based on the total weight of the timber.

|32| A process for producing a timber formulation comprising the following process steps:
  a. providing a timber;
  b. applying an under-atmospheric pressure (vacuum);
  c. contacting the timber with a composition according to any of the embodiments |1|-|19| or a composition obtainable by a process according to any of the embodiments |20|-|29|;
  d. applying an over-atmospheric pressure to the vessel in order to obtain the timber formulation.

|33| a) The process according to embodiment |32|, wherein the vacuum is preferably in a range from 0.01-2.0 bar, more preferably in the range from 0.3-1.5 bar, most preferably in the range from 0.8-1.0 bar.
  b) The process according to embodiment |32|, wherein the under-atmospheric pressure is preferably in a range from 0.01-1.0 bar, more preferably in the range from 0.05-0.99 bar, most preferably in the range from 0.1-0.3 bar.

|34| The process according to any of the embodiments |32|-β3|, wherein the water content of the timber is preferably in a range from 5-50 wt.-%, more preferably in the range from 10-40 wt.-%, most preferably in the range from 18-35 wt.-%, each based on the total weight of the timber.

|35| The process according to any of the embodiments |32|-β4|, wherein the over-atmospheric pressure is preferably in the range from 1-15 bar, more preferably in the range from 2-14 bar and most preferably in the range from 9-11 bar.

|36| The process according to any of the embodiments |32|-|35|, wherein the timber comprises preferably at least 10 wt.-%, more preferably at least 25 wt.-%, most preferably at least 45 wt.-% sapwood, each based on the total weight of the timber.

|37| The process according to any of the embodiments |32|-|36|, wherein the contacting in step c. is performed with a treating solution, wherein the treating solution comprises the composition being diluted by a solution solvent, wherein the concentration of the composition is preferably in the range from 0.05-70 wt.-%, more preferably in the range from 0.08-20 wt.-%, most preferably in the range from 0.1-8 wt.-%, each based on the treating solution. The solution solvent can be any solvent suitable to dilute the composition according to the invention. Preferred solution solvents are these mentioned in the solvent section. Among those water is most preferred.

All aspects and embodiments which have been disclosed pertaining to the composition, the process for producing a composition, the timber formulation and the process for producing a timber formulation, according to the invention also apply to the corresponding features of both the construction and use of a composition according to the invention and vice versa.

|38| A construction comprising a timber formulation according to any of the embodiments |30|-|31| or obtainable by a process according to any of the embodiments |32|-|37|.

|39| The construction according to embodiment |38|, wherein the construction comprises an exterior surface which comprises the timber formulation, according to any of the embodiments |30|-|31| or obtainable by a process according to any of the embodiments |32|-|37|.

|40| The construction according to embodiment |39|, wherein the exterior surface is of a sawed timber, wherein the sawed timber is preferably selected from the group consisting of a deck, a roof, a terrace, a timber-frame, a post, a pole, garden furniture, cladding, or at least two thereof

|41| A use of a composition according to any of the embodiments |1|-|19| or obtained by a process according to embodiments |20|-|29| to protect the exposed surface of a timber.

|42| The use according to embodiment |41|, wherein the timber is part of a wood comprising product.

|43| The use according to embodiments |41|-|42|, wherein the timber is comprised in an exterior surface.

The above embodiments can be combined amongst each other. Each possible combination is herewith a part of the disclosure of the specification.

Timber

Timber according to the invention is all lignin comprising material generally arising from wood, roots, bushes or other natural sources, preferably wood. The lignin content of said material is preferably in the range from 5-50 wt.-%, more preferably in the range from 10-40 wt.-% and most preferably in the range form 15-35 wt.-%, each based on said material. Preferred timbers in the context of the invention belong to any hardwood or softwood family. The preferred timbers are those comprising both heartwood and sapwood. It is preferred that the untreated timbers contain sapwood in the range of 10-90 wt.-% of the timber, more preferably in the range of 20-85 wt.-% of the timber and most preferably in the range of 30-80 wt.-% of the timber. It is further preferred that the wood belongs to the genus of "pinoideae", preferably, to the family of Pinus, most preferably to the family of Yellow pine. It is quite often preferred that the timber formulation according to the invention is produced or provided and then contacted with an adhesive such as glue, mucilage or hot-melt or a combination of at least two thereof. Furthermore, the timber according to the present invention can be of any dimension. A preferred dimension is suited to being placed in a vessel for treating the timber. Therefore, the timber can be a rod, a plank, a chip, saw-dust or a combination of at least two thereof, wherein rods and planks are preferred.

The timber used, is preferably exposed to a cutting step before application of the composition and timber formulation according to the invention begins. The timber is preferably cut into specific shapes and sizes, and preferably stacked in a horizontal orientation. Preferred stacks consist of a plurality of individual timbers in a range preferably from 50-600 pieces, more preferably in a range from 100-500 pieces, most preferably in a range from 200-400 pieces. It is preferred that each piece of timber is itself separated from the closest neighbouring pieces of timber by a vertical distance preferably in a range from 0.1-5 cm, more preferably in a range from 0.2-3 cm, most preferably in a range from 0.5-2 cm; and a horizontal distance preferably in a range from 0.2-5 cm, more preferably in a range from 0.3-4 cm, most preferably in a range from 0.5-1.5 cm. The spacing between each horizontal row is preferably created by inserting smaller pieces of specifically designed timber between each row of horizontally stacked timbers. The vertical spacing is preferably created by controlled orientation of the timber pieces in each row.

Copper Salt

Copper salts (Cu-salts) according to the invention are all types of Cu compounds which comprise copper in ionic form. Cu-salts can be obtained synthetically or occur in the earths crust. Cu is known from the art to be used in wood preservatives. Cu-salts according to the invention can be organic or inorganic Cu-salts, wherein inorganic Cu-salts are preferred. Moreover, water-insoluble Cu-salts are preferred, wherein inorganic water-insoluble metal salts are particularly preferred. Cu-salts can be of the Cu(I), Cu(II) or Cu(III) form. Organic Cu-salts are preferably metal organic copper compounds comprising at least two $C_xH_y$ moieties wherein x and y can be each independently an integer value of 1, 2 or more, such as CuMe, CuEt, CuPr. Other preferred compounds can comprise $C_xH_yO_z$ wherein x can be an integer value in the range preferably from 1-20, more preferably from 2-15, most preferably from 2-11; y can be an integer value in the range preferably from 1-30, more preferably from 3-26, most preferably from 5-23, most preferably from 10-19; and z can be an integer value in the range preferably from 1-6, more preferably from 2-5, most preferably from 2-3. These compounds are preferably of linear or cyclic form, wherein a combination of both is preferred. Preferred compounds comprising this formula are copper naphthenate or copper(II)2-ethylhexanoate or both.

Inorganic Cu-salts preferably comprise an anion selected from the group consisting of $CO_3$, $HCO_3$, $SO_x$, $Cl_2$, $(NO_3)_2$, $(OH)_2$, CN, or a combination of at least two thereof. Preferred Cu-salts are water-insoluble wherein said Cu-salts may be selected from the group consisting of $CuCO_3$, $Cu(HCO_3)_2$, $CuHCO_3$, $Cu(OH)_2.CuCO_3$, CuO. Preferred Cu-salts according to the invention are $CuCO_3$ and $Cu(HCO_3)_2$, $Cu(OH)_2.CuCO_3$, wherein $Cu(OH)_2.CuCO_3$ is particularly preferred and often referred to as basic copper carbonate.

It is further preferred that the inorganic Cu-salt is in a liquid phase comprising a solvent wherein the liquid phase can preferably be a solution or a dispersion, wherein a solution is preferred. It is preferred that the dispersion of Cu-salt is ground in order to obtain a Cu-salt particle size preferably less than 3000 nm, more preferably less than 2000 nm in size, and most preferably less than 1000 nm in size.

Cyclic Organic Compounds

Cyclic compounds consist of a series of atoms which are connected to form a ring. Rings may be of any size and may contain any number of heteroatoms, wherein cyclic compounds comprising at least one heteroatom different to C are preferred and cyclic compounds comprising at least one heteroatom different to C and B are particularly preferred in case of the B-free cyclic organic compounds. Preferably rings can contain 3, 4, 5, 6, 7, 8 or 9 atoms, wherein rings with 5 and 6 atoms are preferred. A ringed structure may contain a plurality of rings joined together, thus forming a macro-cyclic structure. A preferred macro-cyclic structure may contain from 2-20, preferably 2-10 and more preferably 2-3 rings.

All cyclic organic compounds, in particular aromatic and aliphatic compounds are considered suitable under the present invention. It is preferred, however, that at least one of the cyclic compounds used according to the invention, exhibits a degree of delocalization, preferably an aromatic ring structure. It is preferred according to one aspect of the invention that the at least one B free cyclic organic compound comprises at least one aromatic ring. The preferred aliphatic cyclic compounds may contain numerous connected cycles, preferably in a range from 2-6 cycles, and more preferably in a range from 2-4 cycles. The cycles may be preferably 3-12 membered rings, more preferably 4-10 membered rings, most preferably 5-8 membered rings. Each cyclic ring contains preferably between 1-6 heteroatoms, more preferably 2-3 heteroatoms. These heteroatoms are preferably selected from the group consisting of (O, B, N, P or at least two thereof, wherein, B, N or a combination of at least two thereof is preferred.

It is a preferred embodiment that the at least first cyclic organic compound (ii) comprised in the composition has a moiety of the following general formula (I):

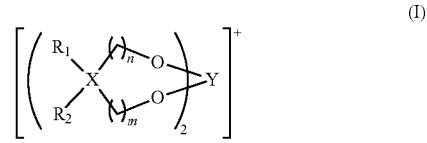

wherein in formula (I)
X is selected from elements; P, N, or B, preferably N;
Y is B;
$R_1$, $R_2$ are independently from each other a saturated linear hydrocarbon containing from 1-20 C atoms, preferably from 5-15 C atoms, more preferably from 8-12 atoms; and
m, n, are independently from each other any integer value in the range from 1-20, it is preferred that n is an integer value in the range from 1-20 and m is an integer value in the range from 1-20; it is more preferred that n is an integer value in the range from 1-10 and m is integer value in the range from 1-10; it is most preferred that n is an integer value in the range from 2-5 and m is an integer value in the range from 2-5.

According to another embodiment of the invention it is preferred that the at least one further cyclic organic compound (iii) has a moiety of the general formula (II):

wherein in formula (II)
R₃ is a heteroatom selected from elements C or N, preferably N;
R₄ is a non-C heteroatom selected from elements, N, O or S, preferably N or O, most preferably N;
R₅ is a heteroatom selected from elements C or N, preferably N;
R₆ is a heteroatom selected from elements, C, N, O or S, preferably C or N, most preferably C; and
R₇ is H, or an organic moiety, wherein the organic moiety can also comprise at least one heteroatom selected from the group of C, H, O, N, halogen, or a combination of least two thereof.

These formulae enable the skilled person to choose suitable compounds in order to carry out the invention.

Betain

Betains, their derivatives, and formulations based on them, are known from the art. Betains are a class of cyclic compound that contain both a cationic functional group and an anionic functional group. "Spiro Compounds" Betains may contain 1 or more cyclic structure. These cyclic structures are connected preferably via a common heteroatom. The number of rings within the overall structure will thus be determined by the valency of the central heteroatom. The included cycles may each independently contain between 3 and 20 atoms, preferably between 4 and 15 atoms, most preferably between 5 and 10 atoms. Quite often there are sidechains connected to the cycles. These side chains are preferably linear hydrocarbons, most preferably saturated linear hydrocarbons comprising a number of C atoms in a range from 1-20 C atoms, more preferably in a range from 5-15 C atoms, most preferably in a range from 8-12 C atoms.

A person skilled in the art would be able to select at least one compound from the group consisting of; decyl betain, alkyl aminobetain, alkyl dimethyl betain, cocamidopropyl betain, glycine betain, 1-decanamine, N-decyl-, oxirane and 1,2-propanediol, alkylpolyethoxy ammonium borate, decyl-polyoxyethyl ammonium borate, di-decyl-poly-oxethyl-ammoninum borate (DPAB), N-methacryloyloxyethyl-N, N-dimethyl ammonium-α N-methylcarboxybetain.methacrylic acid alkyl ester copolymer (also known as polymeric betain), in order to carry out the invention.

Triazole

Triazoles are known from the art to be effective fungicides. They are another class of cyclic compound. Triazoles consist of a 5-membered ring with the molecular formula C₂H₃N₃. A triazole is an isomeric compound with two isomers, 1,2,3-Triazole and 1,2,4-Triazole, wherein the 1,2,4-Triazole is preferred. Triazoles and their derivatives can quite often exhibit delocalization within the cyclic structure.

A skilled person would be able to choose a suitable compound from at least the following, in order to carry out the invention. Preferred triazoles are selected from the group consisting of; (RS)-1-(4-chlorophenyl)-4,4-dimethyl-3-(1H,1,2,4-triazol-1-ylmethyl)pentan-3-ol (tebuconazole), 2-(2,4-difluorophenyl)-1,3-bis(1H-1,2,4-triazol-1-yl)propan-2-ol (fluconazole), {[2-(2,4-difluorophenyl)-1,3-bis(1H-1,2,4-triazol-1-yl)propan-2-yl]oxy}phosphonic acid (fosfluconazole), 1-[4-[[(2S,4S)-2-(2,4-dichlorophenyl)-2-(1,2,4-triazol-1-ylmethyl)-1,3-dioxolan-4-yl]methoxy]phenyl]-4-propan-2-yl-piperazine (terconazole), 2-(2,4-dichlorophenyl)-1-(1H-1,2,4-triazol-1-yl)hexan-2-ol (hexaconazole), 4-{2-[(1R,2R)-(2,5-difluorophenyl)-2-hydroxy-1-methyl-3-(1H-1,2,4-triazol-1-yl)propyl]-1,3-thiazol-4-yl}benzo nitrile (isavuconazole), 1-[[2-(2,4-dichlorophenyl)-4-propyl-1,3-dioxolan-2-yl]methyl]-1,2,4-triazole (propriconazole), 1-(4-Chlorophenoxy)-3,3-dimethyl-1-(1H-1,2,4-triazol-1-yl)-2-butanone (triadimefon), 2-(4-Chlorphenyl)-3-cyclopropyl-1-(1H-1,2,4-triazol-1-yl)bu-tan-2-ol (cyproconazol), (2R,4S)-rel-1-(butan-2-yl)-4-{4-[4-(4-[(2R,4S)-2-(2,4-dichlorophenyl)-2-(1H-1,2,4-triazol-1-ylmethyl)-1,3-dioxolan-4-yl]methoxy}phenyl) piperazin-1-yl]phenyl-4,5-dihydro-1H-1,2,4-triazol-5-one (itraconazole), 4-(4-(4-(4-(((3R,5R)-5-(2,4-difluoro phenyl)-5-(1,2,4-triazol-1-ylmethyl)oxolan-3-yl)methoxy)phenyl)piperazin-1-yl)phenyl)-2-((2S,3S)-2-hydroxypentan-3-yl)-1,2,4-triazol-3-one (posaconazole), (2R,3S)-2-(2,4-difluoro phenyl)-3-(5-fluoropyrimidin-4-yl)-1-(1H-1,2,4-triazol-1-yl)butan-2-ol (voriconazole). The compounds (RS)-1-(4-chlorophenyl)-4,4-dimethyl-3-(1H,1,2,4-triazol-1-ylmethyl)pentan-3-ol, or (tebuconazole) and 1-[[2-(2,4-dichlorophenyl)-4-propyl-1,3-dioxolan-2-yl]methyl]-1,2,4-triazole (propriconazole), are the most preferred triazoles according to the invention.

Furthermore, triazoles are an example of B free cyclic organic compounds. It is preferred according to the invention that the triazole compounds used are selected from the group consisting of; triadimefon, cyproconazol, tebuconazol, propriconazole or salts of each thereof. It is further preferred that the at least two different further B free cyclic organic compounds are obtained by contacting at least a first and a second B free cyclic organic compound.

Composition

The composition according to the invention is designed as a wood preservative. The composition may be used as part of a timber treatment, or may be used as part of a timber formulation which is used as part of a timber treatment. The composition according to the invention comprises as composition constituents;
  i. a Cu-salt
  ii. at least one first cyclic organic compound comprising a B heteroatom in a cycle;
  iii. at least one further B free cyclic organic compound comprising a heteroatom selected from the group of O, N, S, or P, or a combination of at least two thereof in a cycle. Preferred heteroatoms are N, S or O, with N and O being most preferred.

It is a preferred embodiment of the present invention that the composition according to the invention comprises copper (i) preferably in a range from 0.02-80 wt.-%, more preferably in a range from 0.05-75 wt.-%, most preferably in a range from 0.1-70 wt.-%.

It is further preferred that the composition according to the invention comprises a solvent, wherein the solvent is preferably polar and selected from the group of; ketones, amines, alcohols, carboxylic acids, esters or a combination of at least two thereof. Furthermore, the solubility of the constituents could be enhanced by appropriate enhancers. These enhancers are preferably selected from the group consisting of; surfactants, soaps, detergents, or a combination of at least two thereof. It is further preferred that the solvent is a polar protic solvent, wherein water and any monoalcohol amine are the most preferred solvent choices.

Process for Producing a Composition

A process for producing a composition according to the invention comprises the following steps;
  i. providing a first cyclic organic compound comprising a B heteroatom;
  ii. providing at least one further B free cyclic organic compound comprising a heteroatom selected from the group of O, N, S, or P, or a combination of at least two thereof, preferably O or N and more preferably O and N, in a cycle;
  iii. providing a Cu-salt;

iv. contacting the first cyclic organic compound comprising a B heteroatom with the at least one further B free cyclic organic compound in a solvent in order to obtain a solution;

v. contacting the solution of step (iv) with a Cu-salt in order to obtain the composition;

wherein the composition can be used as a treating solution for preserving a timber.

The at least one further B free cyclic organic compound can be selected from the group consisting of triadimefon, cyproconazol, tebuconazol, propriconazole or salts of each thereof, wherein tebuconazol and propriconazole are preferred. It is further preferred that at least two different further B free cyclic organic compounds are used. These two compounds are obtained by contacting at least a first and a second B free cyclic organic compound. This contacting is preferably performed prior to the contacting of step iv., and at a temperature preferably in the range from 30-80° C., more preferably in the range from 35-75° C. and most preferably in the range from 40-60° C.

During this process for producing a composition according to the invention, the first cyclic compound comprising a B heteroatom and the at least two further B free cyclic compounds are contacted prior to the contacting with Cu-salt. The two B free cyclic organic compounds are first contacted at temperatures in a range preferably from 30-80° C., more preferably in the range from 35-75° C. and most preferably in the range from 40-60° C. Once this contact has been made, then contact with the first cyclic compound comprising a B heteroatom can occur, wherein said cyclic organic compound comprising B, has an active ingredient (AI) concentration of preferably at least 30% and preferably not in excess of 80%.

Contact between these respective solutions occurs at concentrations in a range preferably from 1:5, wherein 1 is the concentration of the first cyclic organic compound comprising a B heteroatom and 5 is the concentration of the at least one further B free cyclic organic compound, it is more preferred that they are contacted in a ratio of 1:10, with the most preferred ratio being 1:25. This contacted solution is cooled to a temperature preferably in the range from 10-50° C., more preferably in the range from 15-30° C., most preferably in the range from 18-28° C., prior to contacting with the Cu-salt.

The Cu-salt is preferably comprised in a liquid phase, wherein the liquid phase can preferably be a solution or a dispersion, wherein a solution is preferred. Examples herein, include a Cu-salt in a solution of solvent with its pH adjusted to lie in a range preferably from 7.5-14.0, more preferably from 7.8-12.0, most preferably from 8.0-10.0. The Cu-salt solution is then added to the aforementioned contacted solution (see example 1). Another example describes a dispersion of Cu-salt in a solvent which is further treated via a grounding process before contacting the aforementioned contacted solution (see example 2). It is preferred that preparation of the Cu-salt occurs at ambient temperatures. The above-described examples of preparing a Cu-salt in a liquid phase, and all possible variations thereof, are comprised within this invention.

The Cu-salt can be ground at any stage of the process for preparing the composition according to the invention. It is, however, preferred to grind the Cu-salt in or after step iii. of the process for producing the composition according to the invention. It is most preferred to conduct the grinding in or after step iv. in the process for producing a composition according to the invention. It is further preferred that the grounding process produces Cu-particles wherein at least 50 wt.-%, more preferably at least 60 wt.-%, most preferably at least 70 wt.-%, of them are preferably less than 2000 nm in size, more preferably less than 1500 nm in size, most preferably less than 1000 nm in size, and, wherein less than or equal to 30 wt.-%, of the particles are smaller than 100 nm in size, preferably less than or equal to 20 wt.-%, are smaller than 100 nm in size and most preferably less than or equal to 10 wt.-%, are smaller than 100 nm in size.

Once the components of steps (i)-(iii) are prepared according to their respective processes, contact of the respective components is made under constant stirring at ambient temperature and pressure, wherein step (i) and (ii) are contacted together prior to the contacting in step (iii), in order to produce the composition according to the invention. Said composition can be further used as a treating solution for a timber comprised in a timber formulation.

Process for Producing a Timber Formulation

A further embodiment of this invention is a process for producing a timber formulation comprising the above composition. The timber formulation together with the process in which it is applied, produce a preserved timber which is suitable for construction use. This process has the following stages:

a) providing a timber; preferably a timber with at least 60 wt.-% sapwood, more preferably at least 65 wt.-% sapwood, most preferably at least 80 wt.-% sap-wood, wherein the wt.-% values can apply to both softwood or hardwood timbers. It is preferred that the heartwood content is less than 20 wt.-% of the timber, b) introducing the timber to a vessel;

c) applying an under-atmospheric pressure (vacuum) in a range from 0.01-2.0 bar to the vessel, preferably wherein the pressure is in a range from 0.01-1.0 bar, more preferably in the range from 0.05-0.99 bar, most preferably in the range from 0.1-0.3 bar;

d) contacting the timber with a composition according to the invention in order to obtain a contacted timber;

e) applying an over-atmospheric pressure, in the range from 1-15 bar to the vessel.

Initially the timber is exposed to a vacuum in the range preferably from 0.01-2.0 bar, more preferably in a range from 0.3-1.5 bar, most preferably in a range from 0.8-1.0 bar. The timber is exposed to this vacuum for a time period ranging from 5-500 minutes, more preferably from 10-250 minutes, most preferably from 20-100 minutes. Upon completion of this initial treatment step, a treating solution comprising the composition according to the invention or obtained by the process according to the invention, is sucked into the vessel. This uptake of composition is controlled by at least one valve mechanism, preferably at least two valve mechanisms which are connected to a cylindrical tubing positioned within the vessel (see FIG. 3). No more than 5 valve mechanisms are used. The next stage in treatment requires the pressure in the vessel to be increased, preferably in a range from 1-15 bar, more preferably in a range from 2-14 bar, most preferably in a range from 9-11 bar. It is further preferred that this increase in pressure is held for a time period ranging from 10-1000 minutes, more preferably from 20-500 minutes, most preferably from 50-150 minutes. After this time period, the pressure is reduced to ambient pressure and the treating solution comprising the composition according to the invention or obtained from the process according to the invention is removed from the vessel. The impregnated contacted timbers are dried at ambient temperature. The exterior surroundings of the vessel during the treatment process are preferably subjected to normal atmospheric conditions.

Vessel

The vessel used according to the invention, is preferably used for the purpose of reducing the amount of solvent present in the composition and to achieve a preferably dried contacted timber. The vessel is preferably a metal chamber, wherein the metal can be of pure or alloy form. The chamber according to the invention can be comprised of at least one of the materials selected from the group consisting of iron, copper, zinc, nickel, aluminum, tin, titanium, niobium, or alloys of at least any one metal thereof. Alloys of iron are particularly preferred. It is also preferred that the chamber can be sealed, and is preferably capable of withstanding high pressures. It is further preferred that the chamber has a circular or rectangular cross section, with circular being most preferred. There is at least one point of entry into the vessel for the timbers to be placed inside and subsequently treated with preferably both a vacuum and an over-atmospheric pressure.

The vacuum applied to the interior of the vessel is preferably in the range from 0.01-2.0 bar, more preferably in a range from 0.3-1.5 bar, most preferably in a range from 0.8-1.0 bar. The vacuum is applied preferably for no longer than 100 minutes to the timber.

The under-atmospheric pressure (vacuum) applied to the interior of the vessel is preferably in the range from 0.01-1.0 bar, more preferably in the range from 0.05-0.99 bar, most preferably in the range from 0.1-0.3 bar. The under-atmospheric pressure (vacuum) is applied preferably for no longer than 100 minutes to the timber.

The over-atmospheric pressure applied to the interior of the vessel preferably ranges from 1-15 bar, more preferably ranges from 2-14 bar, most preferably ranges from 5-12 bar. It is preferred that the over-atmospheric pressure exposure lasts no longer than 500 minutes. The exterior of the vessel is preferably subjected to normal atmospheric pressure and temperature.

Construction

It is an object of this invention to provide a protected timber material wherein said protected timber material may be used for construction purposes.

The construction preferably comprises a construction exterior, wherein the construction exterior comprises the timber formulation and is also the part of the construction which is subject to weathering.

Constructions according to the invention, are not limited to constructions that use only timber. Timbers according to this invention can be applied to constructions that use timber as a starting or base material in combination with other materials.

Constructions according to the invention, may also be used as the finishing material to a construction, e.g. an exterior façade, doors/doorways, flooring, a balcony, a deck. The construction can also be contained and thus shielded from weathering, however it may be exposed to other pressures. For example, the timbers may be used for purposes such as staircases or other furnishings.

Uses of such constructions preferably range from the commercial to the domestic market. The constructions can preferably be selected from the group comprising; decking, roofing, housing—for both interior (e.g. timber-frame) and exterior use, furniture—for both interior and exterior use, indoor and outdoor recreational areas.

DESCRIPTION OF DRAWINGS

The drawings are for illustrative purposes only, they are not a scale representation of the invention and are not to be considered as limiting the scope of the invention. The figures show in:

FIG. 1 is a process flow diagram describing the process according to the invention from composition preparation through to timber testing. The steps followed are:

I. contacting a first B comprising cyclic organic compound with at least one further B free cyclic organic compound in order to obtain a solution;
II. preparing a liquid-phase Cu-salt;
III. contacting, at ambient temperature, solution I with liquid-phase II in order to obtain the composition according to the invention;
IV. timber appropriately spaced via separators, placed in a vessel;
V. vacuum of 0.1 bar is applied to the vessel for 30 minutes at 25° C.;
VI. composition of III. is introduced to the vessel;
VII. over-atmospheric pressure of 10 bar is applied to the vessel for 90 minutes at 25° C. in order to obtain treated timber;
VIII. pressure returned to ambient pressure and composition of III. is removed from the vessel;
IX. the treated timber is dried at ambient temperature.

Figure 1:
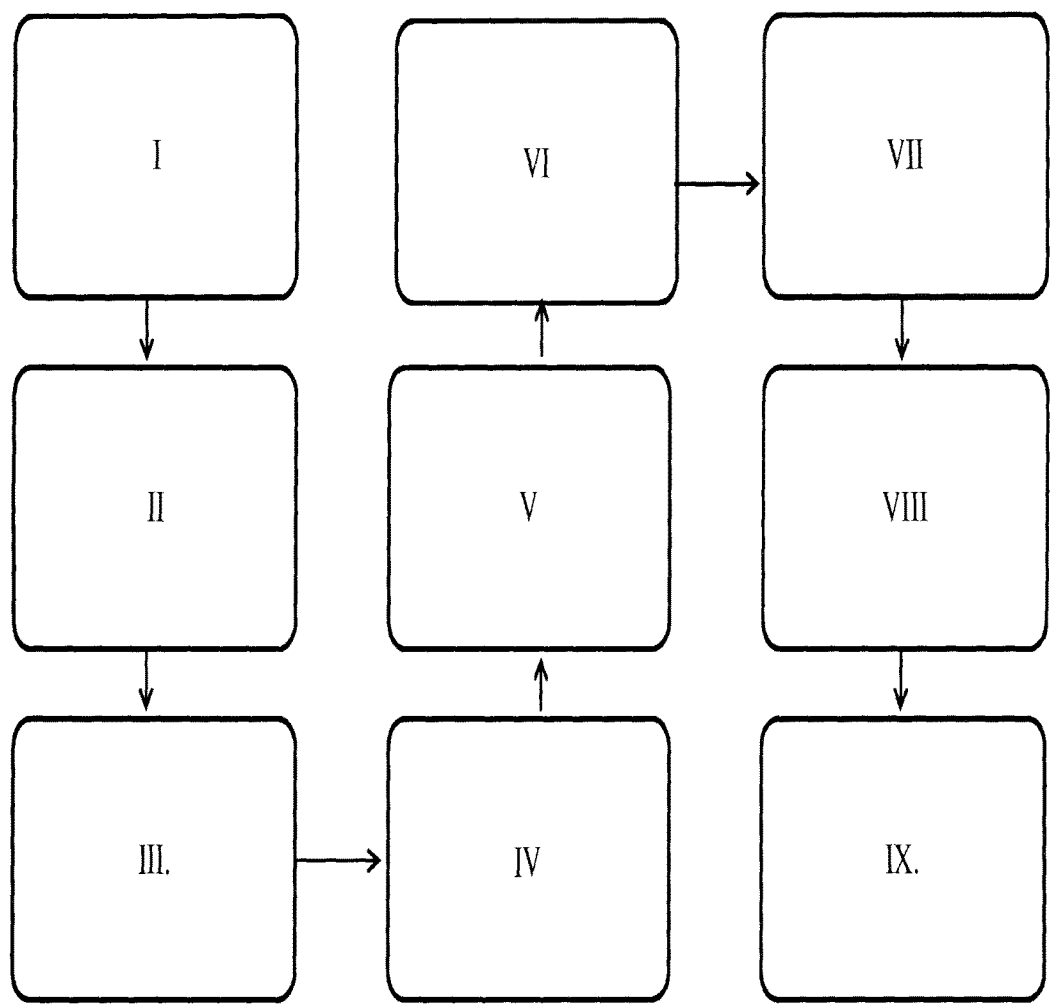
FIG. 1 a process flow diagram of the process according to the invention.
Figure 2:
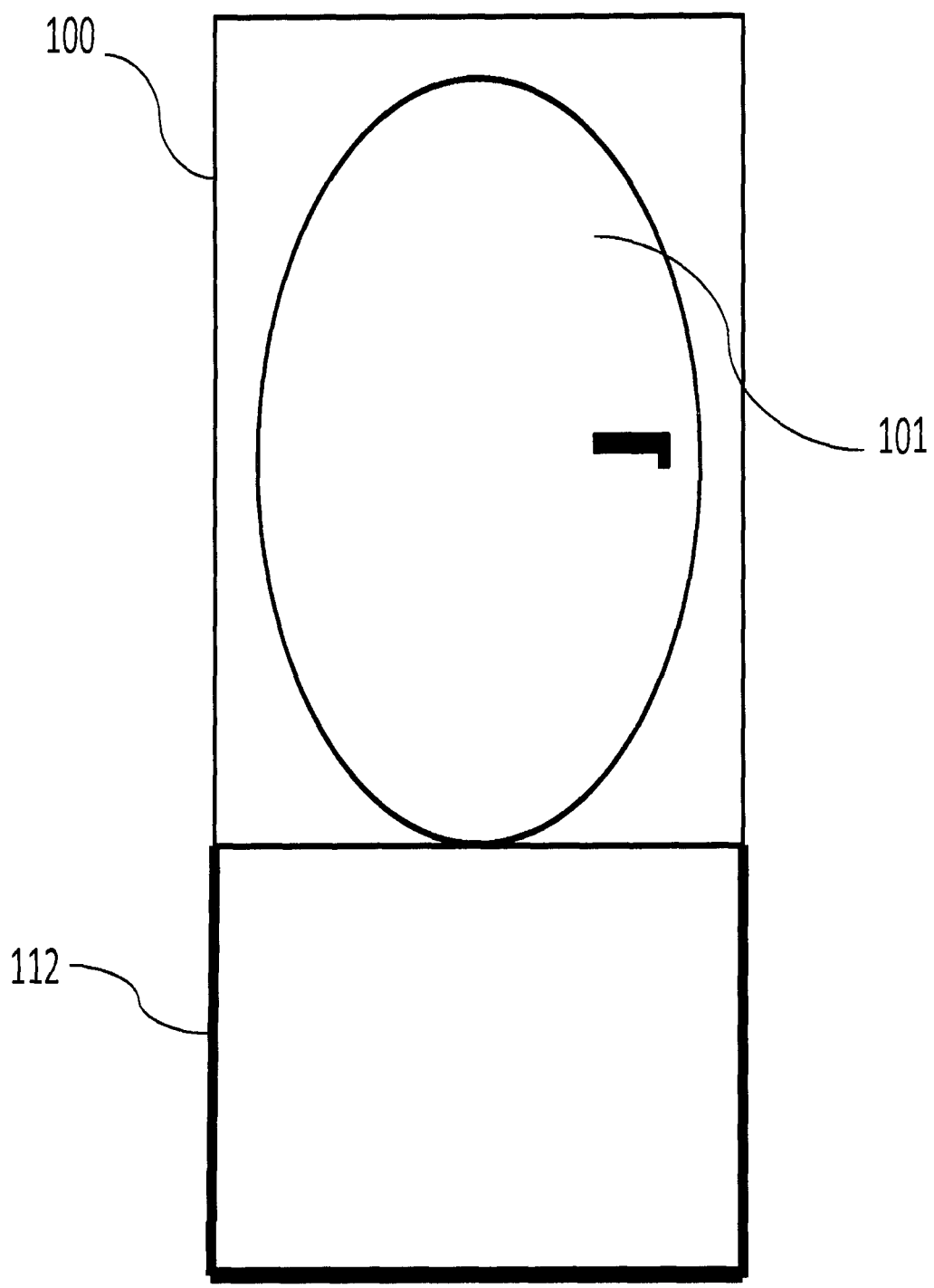
FIG. 2 a schematic drawing showing the exterior of a vessel and compartment used according to the invention.

FIG. 2 shows a vessel 100 closed by a door 101 situated above a compartment 112.

Figure 3:
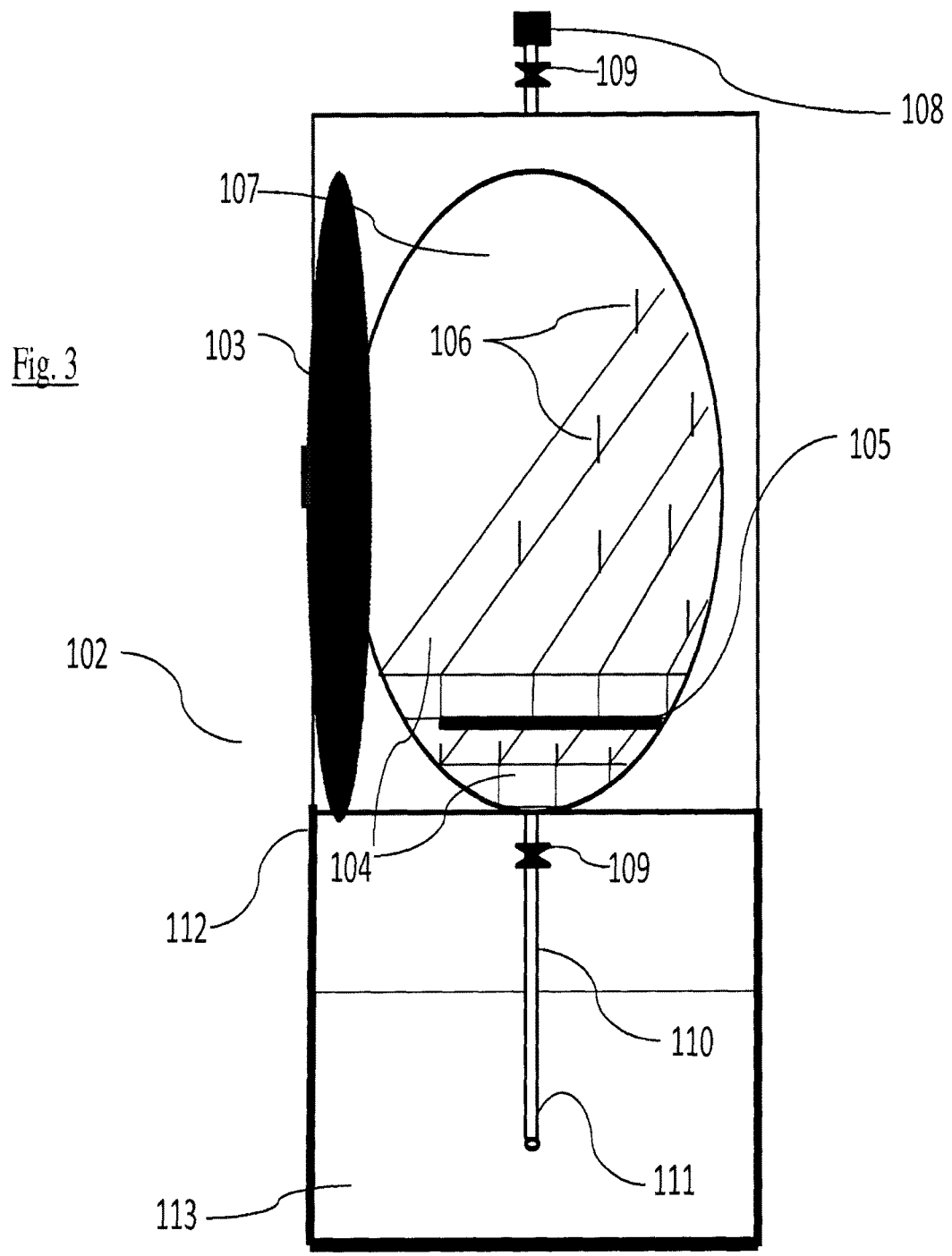
FIG. 3 a schematic drawing of an open vessel with compartment comprising the composition according to the invention.

FIG. 3 shows a vessel under working conditions 102 with an open door 103 allowing an interior view 107 of both the vessel 100 and compartment 112. Inside the vessel 107 are timbers 104, with said timbers 104 being separated horizontally by a separator 105 and vertically by separators 106. The vessel 100 is positioned above compartment 112 wherein the composition according to the invention 113 is stored during the treatment process. The composition 113 is transported into the vessel 100 via an opening 111 in the cylindrical tubing 110 positioned within the vessel 100, wherein said cylindrical tubing 110 comprises two valve mechanisms 109 and a seal 108. By adjusting the valve mechanisms 109 and the pressure applied to the interior of the vessel 107, the composition 113 is transported from the compartment 112 to the interior of the vessel 107 and the timbers 104 are treated.

Figure 4:
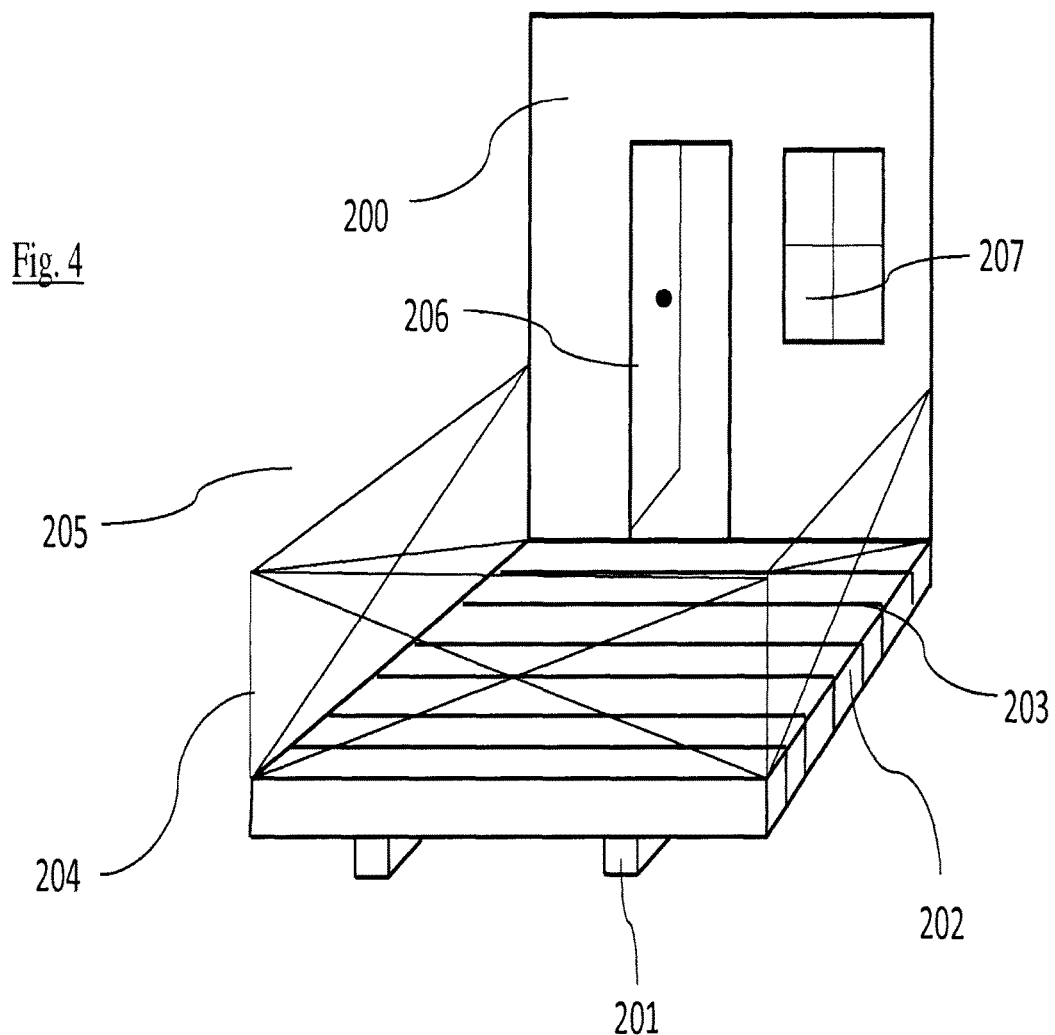
FIG. 4 a schematic representation of a deck.

FIG. 4 is a representation of a deck 205 extending from the exterior wall of a construction 200, with said wall comprising both a door 206 and window 207. The deck is comprised of horizontal timbers 202 joined together at interfaces 203. Said joined timbers 202 are supported by perpendicular timbers placed underneath 201. The deck is finished by a timber railing 204 wherein said timbers share interfaces primarily at the vertices and edges of the horizontal timbers 202. It should be noted that this figure is a general representation of a deck and is for illustration purposes only. Decks of various sizes, designs and other variables are herein also included.

EXAMPLES

The invention is now explained by means of examples which are intended for illustration purposes only and are not to be considered as limiting the scope of the invention. In particular the timbers prepared according to the invention and the examples herein described, are for illustration purposes only. There are numerous possible combinations of reaction conditions applicable to this invention. The selected examples are chosen to give a general, yet detailed description of results and are not to be considered as limiting the scope of the invention.

Example 1

Product A—Dissolved Copper

Solution I

At room temperature, 200.0 g of basic copper carbonate (CAS number 12069-69-1) was slowly dissolved in a solution of 371.0 g of monoethanol amine (commercially available from Aldrich) in 236.5 g water under vigorous stirring. Once the copper carbonate completely dissolved, the pH value of the solution was adjusted with carbon dioxide to 8.8-9.0.

Solution II

At 50° C., a solution of 2.0 g of propiconazol (CAS number 60207-90-1) in 2.0 g propylene glycol (commercially available from Aldrich) and 2.0 g tebuconazol (CAS number 107534-96-3) were added to 100.0 g di-decyl-poly-oxethyl-ammoninum borate (CAS number 214710-34-6) and stirred until completely dissolved.

After cooling solution II to room temperature, solution II was added slowly to solution I under continuous stirring in order to obtain a homogeneous solution, hereinafter referred to as Product A. The Product A contained 33.3 wt.-% Active Ingredient (AI). The AI contained 33.3 wt.-% copper.

Table 1 shows the reactants of product A and their respective amounts, whilst table 2 gives the active ingredients and their respective amounts.

TABLE 1

| Compounds | Amount [g] | Normalized [%] |
|---|---|---|
| Copper carbonate 50% | 200.00 | 21.89% |
| MEA | 371.00 | 40.61% |
| Water | 236.50 | 25.89% |
| Propiconazol | 2.00 | 0.22% |
| Propylene glycol | 2.00 | 0.22% |
| Tebuconazol | 2.00 | 0.22% |
| DPAB TGAI | 100.00 | 10.95% |
| Product A | 913.50 | 100.00% |

MEA = monoethanolamine,
DPAB = Crude betain with an AI content of 59%,
TGAI = Technical grade AI,
AI = the active ingredient,
DPAB TGAI = DPAB 59% AI - only 59% are active AI.

The ratios of copper:azol, copper:betain and betain:azol were 1:25, 1:1 and 1:25 respectively, wherein the azol is the sum of propiconazol and tebuconazole. The copper content based on the amount of copper oxide is 33.3%.

TABLE 2

| Actives | Amount [g] | Normalized [%] |
|---|---|---|
| Copper oxide | 125.16 | 66.52% |
| DPAB 59% AI | 59.00 | 31.36% |
| Propiconazol | 2.00 | 1.06% |
| Tebuconazol | 2.00 | 1.06% |
| Product A | 188.16 | 100.00% |

DPAB = Crude betain with an AI content of 59%,
TGAI = Technical grade AI,
AI = the active ingredient,
DPAB TGAI = DPAB 59% AI - only 59% are active AI.

Example 2

Product B—Micronized Copper

Dispersion I 400.0 g of copper carbonate (CAS number 12069-69-1) was dispersed in a solution of 144.0 g of water. After stirring for 30 min the mixture was placed in a commercial grinding mill and ground until 70 wt.-% or more of the particles were less than 1000 nm in size, and 10 wt.-% or less of the particles, were smaller than 100 nm in size.

Solution II

At 50° C., a solution of 4.0 g of propiconazol (CAS number 60207-90-1) in 4.0 g, propylene glycol (commercially available from Aldrich) and 4.0 g tebuconazol (CAS number 107534-96-3) were added to 200.0 g di-decyl-poly-oxethyl-ammoninum borate (CAS number 214710-34-6) and stirred until the dissolving process was complete and a homogeneous solution was obtained.

After cooling solution II to room temperature, solution II was added slowly to dispersion I under continuous stirring in order to obtain a homogeneous dispersion hereinafter referred to as Product B. The Product B contained 80.4 wt.-% Active Ingredient (AI). The AI contained 33.3 wt.-% copper.

Table 3 shows the reactants of Product B and their respective amounts, whilst table 4 gives the active ingredients and their respective amounts.

TABLE 3

| Compounds | Amount [g] | Normalized [%] |
|---|---|---|
| Copper carbonate 50% | 400.00 | 52.91% |
| Water | 144.00 | 19.05% |
| Propiconazol | 4.00 | 0.53% |
| Propylene glycol | 4.00 | 0.53% |
| Tebuconazol | 4.00 | 0.53% |
| DPAB TGAI | 200.00 | 26.46% |
| Product B | 756.00 | 100.00% |

DPAB = Crude betain with an AI content of 59%,
TGAI = Technical grade AI,
AI = the active ingredient,
DPAB TGAI = DPAB 59% AI - only 59% are active AI.

MEA=monoethanolamine, DPAB=Crude betain with an AI content of 59%, TGAI=Technical grade AI, AI=the active ingredient, DPAB TGAI=DPAB 59% AI—only 59% are active AI.

The ratios of copper:azol, copper:betain and betain:azol were 1:25, 1:1 and 1:25 respectively, wherein the azol is the sum of propiconazol and tebuconazole. The copper content based on the amount of copper oxide is 33.3%.

TABLE 4

| Actives | Amount [g] | Normalized [%] |
|---|---|---|
| Copper oxide | 250.31 | 66.52% |
| DPAB 59% AI | 118.00 | 31.36% |
| Propiconazol | 4.00 | 1.06% |
| Tebuconazol | 4.00 | 1.06% |
| Product B | 376.31 | 100.00% |

DPAB = Crude betain with an AI content of 59%,
TGAI = Technical grade AI,
AI = the active ingredient,
DPAB TGAI = DPAB 59% AI - only 59% are active AI.

Example 3

Product C—Betain & Triadimefon

At 50° C., 14.0 g of triadimefon and 36.0 g of water were added to 950.0 g di-decyl-poly-oxethyl-ammoninum borate (CAS number 214710-34-6) and stirred until completely dissolved in order to obtain a homogeneous solution, hereinafter referred to as Product C.

Unlike products A and B, product C contained 0.00 wt.-% copper.

Table 5 shows the reactants of product C and their respective amounts, whilst table 6 gives the active ingredients and their respective amounts.

TABLE 5

| Compounds | Amount [g] | Normalized [%] |
|---|---|---|
| Water | 36.00 | 3.60% |
| Triadimefon | 14.00 | 1.40% |
| DPAB TGAI | 950.00 | 95.00% |
| Product C | 1000.00 | 100.00% |

Triadimefon = triazole, i.e. an N-heterocycle,
DPAB = Crude betain with an Al content of 59%,
TGAl = Technical grade Al,
Al = the active ingredient,
DPAB TGAl = DPAB 59% Al - only 59% are active Al.

The ratios of copper:azol, copper:betain and betain:azol were 0:0, 0:0 and 1:67.86 respectively, wherein the azol is triadimefon.

TABLE 6

| Actives | Amount [g] | Normalized [%] |
|---|---|---|
| DPAB TGAI | 950.00 | 98.55% |
| Triadimefon | 14.00 | 1.45% |
| Product C | 964.00 | 100.00% |

Triadimefon = triazole, i.e. an N-heterocycle,
DPAB = Crude betain with an Al content of 59%,
TGAl = Technical grade Al,
Al = the active ingredient,
DPAB TGAl = DPAB 59% Al - only 59% are active Al.

Example 4

Product D—Betain & Cyproconazol

At 50° C., 3.0 g of cyproconazol and 497.0 g of water were added to 500.0 g di-decyl-poly-oxethyl-ammoninum borate (CAS number 214710-34-6) and stirred until completely dissolved in order to obtain a homogeneous solution, hereinafter referred to as Product D.

As in product C, product D also contained 0.00 wt.-% copper.

Table 7 shows the reactants of product D and their respective amounts, whilst table 8 gives the active ingredients and their respective amounts.

TABLE 7

| Compounds | Amount [g] | Normalized [%] |
|---|---|---|
| Water | 497.00 | 49.70% |
| Cyproconazol | 3.00 | 0.30% |
| DPAB TGAI | 500.00 | 50.00% |
| Product D | 1000.00 | 100.00% |

DPAB = Crude betain with an Al content of 59%,
TGAl = Technical grade Al,
Al = the active ingredient,
DPAB TGAl = DPAB 59% Al - only 59% are active Al.

The ratios of copper:azol, copper:betain and betain:azol were 0:0, 0:0 and 1:166.67 respectively, wherein the azol is cyproconazol.

TABLE 8

| Actives | Amount [g] | Normalized [%] |
|---|---|---|
| DPAB TGAI | 500.00 | 99.40% |
| Cyproconazol | 3.00 | 0.60% |
| Product D | 503.00 | 100.00% |

DPAB = Crude betain with an Al content of 59%,
TGAl = Technical grade Al,
Al = the active ingredient,
DPAB TGAl = DPAB 59% Al - only 59% are active Al.

Comparative Example

For comparison the product NatureWood-CA, commercially available from Osmose Inc., USA was employed. The NatureWood-CA contained as Active Ingredient (AI): 50 parts by weight basic copper carbonate (CAS number 12069-69-1) to 1 part by weight tebuconazole (CAS number 107534-96-3) to 1 part by weight propiconazole (CAS number 60207-90-1) and no di-decyl-poly-oxethyl-ammoninum borate (CAS number 214710-34-6). See table 9.

TABLE 9

| Compounds | Amount [g] | Normalized [%] |
|---|---|---|
| Copper carbonate 50% | 50.00 | 96.15% |
| Propiconazol | 1.00 | 1.92% |
| Tebuconazol | 1.00 | 1.92% |
| Comparative example | 52.00 | 100.00% |

The ratios of copper:azol, copper:betain and betain:azol were 1:25, 0:0 and 0:0 respectively, wherein the azol is the sum of propiconazol and tebuconazole. Table 10 gives the active ingredients and their respective amounts. The copper content based on the amount of copper oxide is 49.3%.

TABLE 10

| Actives | Amount [g] | Normalized [%] |
|---|---|---|
| Copper oxide | 31.29 | 93.99% |
| Propiconazol | 1.00 | 3.00% |
| Tebuconazol | 1.00 | 3.00% |
| Comparative example | 33.29 | 100.00% |

Preparation of Timbers Using Products A-D/Comparative

Timber pieces were positioned in a treating vessel. Over a period of 30 minutes a pressure of 0.1 bar was applied. The treating solution containing a Product was sucked into the vessel. Then the pressure in the vessel was increased to 10 bar at 25° C. for 90 minutes. Afterwards the pressure was set to ambient pressure and the remainder of the treating solution was removed. The impregnated timber pieces were dried at ambient temperature. Further details are given in the tables and standards below.

Test E7-9 on Product B

The timber employed in the tests was Southern yellow pine. The Standards of the American Wood Protection Association were applied for the test E7-09 as amended in 2009, E18-06 as revised in 2006 and E16-09 as amended in 2009. The details are provided in table 11 below.

The timber employed in the tests was Southern yellow pine. The Standards of the American Wood Protection Association were applied for the test E7-09 as amended in 2009 (tables 11A and 11B), E18-06 as revised in 2006 (tables 12A and 12B) and E16-09 as amended in 2009 table 12C). The details of all tests are provided in the tables below.

TABLE 11A

| Product | Conc. of treating solution [wt.-% AI in water] | Av. absorption of treating solution in timber [l/m³] | Av. AI retention in timber [kg/m³] | Av. copper oxide retention in timber [kg/m³] | Av. DPAB retention in timber [kg/m³] | Av. propiconazol retention in timber [kg/m³] | Av. tebuconazol retention in timber [kg/m³] | Av. rating test site Hawaii |
|---|---|---|---|---|---|---|---|---|
| Product B | 0.400% | 641 | 2.56 | 1.71 | 0.80 | 0.03 | 0.03 | 9.40 |
| Comparative MCA-C | 0.371% | 690 | 2.56 | 2.41 | 0 | 0.08 | 0.08 | 9.55 |

TABLE 11B

| Product | Av. rating after 2 years test site Hawaii | Av. rating after 3 years test site Hawaii | Av. rating after 5 years test site Hawaii | Av. rating after 2 years test site North Carolina |
|---|---|---|---|---|
| Product B | 9.40 | 9.50 | 8.56 | 9.85 |
| Comparative MCA-C | 9.55 | 9.60 | 8.75 | 10.00 |

Tables 11A and 11B show that Product B is sufficiently active to achieve similar results to those obtained from the comparative example. Product B however, is able to retain DPAB to 0.80 kg/m³ whereas the comparative example cannot retain DPAB at all (0.00 kg/m³).

Tables 11A and 11B further show that Product B, with a significantly reduced amount of copper (1.71 kg/m³) compared to the amount of copper in the comparative example (2.14 kg/m³), is capable of achieving a similar level of preservation as that of the comparative example. The E18-09 test produced even better results as can be seen in tables 12A and 12B.

TABLE 12A

| Product | Conc. of treating solution [wt.-% AI in water] | Av. absorption of treating solution in timber [l/m³] | Av. AI retention in timber [kg/m³] | Av. copper oxide retention in timber [kg/m³] | Av. DPAB retention in timber [kg/m³] | Av. propiconazol retention in timber [kg/m³] | Av. tebuconazol retention in timber [kg/m³] | Av. rating test site North Carolina |
|---|---|---|---|---|---|---|---|---|
| Product B | 0.167% | 637 | 1.06 | 0.71 | 0.33 | 0.01 | 0.01 | 10.00 |
| Comparative MCA-C | 0.167% | 647 | 1.08 | 1.02 | 0 | 0.03 | 0.03 | 9.90 |

TABLE 12B

| Product | Av. rating after 2 years test site Hawaii | Av. rating after 5 years test site Hawaii | Av. rating after 2 years test site North Carolina |
|---|---|---|---|
| Product B | 9.60 | 8.85 | 10.00 |
| Comparative MCA-C | 9.70 | 9.17 | 9.90 |

Here it can be seen that less copper and azol are required compared to the corresponding values in table 11, yet the average rating result is higher, at 10.00 compared to 9.40 in table 11.

Here it can be seen that less copper and azol are required compared to the corresponding values in tables 11A and 11B, yet the average rating result is higher, at 10.00 (table 12B) compared to 9.40 in table 11B.

From tables 12A and 12B, Product B, again with a significantly reduced amount of copper (0.71 kg/m³) compared to the amount of copper in the comparative example (1.02 kg/m³), is capable of achieving a similar level of preservation as that of the comparative example, and indeed outperforms the comparative example in the average rating test (after 2 years, test site in North Carolina).

TABLE 12C

| Product | Conc. of treating solution [wt.-% AI in water] | Av. absorption of treating solution in timber [l/m³] | Av. AI retention in timber [kg/m³] | Av. copper oxide retention in timber [kg/m³] | Av. DPAB retention in timber [kg/m³] | Av. propiconazol retention in timber [kg/m³] | Av. tebuconazol retention in timber [kg/m³] | Av. rating after 2 years test site North Carolina |
|---|---|---|---|---|---|---|---|---|
| Product B | 0.167% | 573 | 0.96 | 0.64 | 0.30 | 0.01 | 0.01 | 9.50 |

TABLE 12C-continued

| Product | Conc. of treating solution [wt.-% AI in water] | Av. absorption of treating solution in timber [l/m$^3$] | Av. AI retention in timber [kg/m$^3$] | Av. copper oxide retention in timber [kg/m$^3$] | Av. DPAB retention in timber [kg/m$^3$] | Av. propiconazol retention in timber [kg/m$^3$] | Av. tebuconazol retention in timber [kg/m$^3$] | Av. rating after 2 years test site North Carolina |
|---|---|---|---|---|---|---|---|---|
| Comparative MCA-C | 0.167% | 585 | 0.98 | 0.92 | 0 | 0.03 | 0.03 | 9.61 |

Table 12C shows similar results, i.e., Product B is capable of achieving a similar level of preservation (9.50) as that of the comparative example (9.61). Product B achieves this, however, not only with a lower amount of copper present (0.64 kg/m$^3$ compared to 0.92 kg/m$^3$), but also with a lower absorption of the treating solution itself (573 l/m$^3$ (prod. B) compared to 585 l/m$^3$ (comparative). These are significant and unexpected findings.

Test EN113 on Product C

In both tables 13 and 14 the standard applied is EN113. Prior to EN113, the timber was washed according to EN84. The type of timber used was pine.

Tables 13 and 14 show the average retention of the active ingredient (AI) in Product C when it is exposed to both "poria placenta" (table 13) and "coniophora puteana" (table 14). Comparisons are also made with retention values of DPAB and the azol (triadimefon) in the timber. Average AI retention values are required in order to pass the EN113 Standard.

TABLE 13

| Product | Average a.i. retention against *poria placenta* [kg/m$^3$] | Average DPAB retention in timber [kg/m$^3$] | Average azol retention in timber [kg/m$^3$] |
|---|---|---|---|
| DPAB TGAI | | 4.50 | |
| azol | | | 0.10 |
| Product C | 1.83 | 1.80 | 0.03 |

DPAB = Crude betain with an Al content of 59%,
TGAl = Technical grade Al,
Al = the active ingredient,
DPAB TGAl = DPAB 59% Al - only 59% are active Al.

Table 13 shows that when using Product C, an AI retention value of 1.83 can be achieved with using less DPAB (1.80 kg/m$^3$ instead of 4.50 kg/m$^3$) and less azol (0.03 kg/m$^3$ instead of 0.10 kg/m$^3$).

TABLE 14

| Product | Average a.i. retention against *coniophora puteana* [kg/m$^3$] | Average DPAB retention in timber [kg/m$^3$] | Average azol retention in timber [kg/m$^3$] |
|---|---|---|---|
| DPAB TGAI | | 7.40 | |
| azol | | | 0.10 |
| Product C | 2.89 | 2.85 | 0.04 |

DPAB = Crude betain with an Al content of 59%,
TGAl = Technical grade Al,
Al = the active ingredient,
DPAB TGAl = DPAB 59% Al - only 59% are active Al.

Table 14 shows similar results, with an AI retention value of 2.89 when using smaller amounts of both cyclic compounds DPAB (2.85 kg/m$^3$ instead of 7.40 kg/m$^3$) and azol (0.04 kg/m$^3$ instead of 0.10 kg/m$^3$). These findings show that by reducing the amounts of DPAB and azol by factors of 2.5 and 10 respectively; results are improved, furthermore, they are improved in the absence of copper.

Test EN113 on Product D

In both tables 15 and 16 the standard applied is EN113. Prior to EN113, the timber was washed according to EN84. The type of timber used was pine.

As for product C, tables 15 and 16 show the average retention of the active ingredient (AI) in Product D when it is exposed to both "poria placenta" (table 15) and "coniophora puteana" (table 16). Comparisons are also made with retention values of DPAB and the azol (cyproconazol) in the timber. The average AI retention values are required in order to pass the EN113 Standard.

TABLE 15

| product | Average a.i. retention against *poria placenta* [kg/m$^3$] | Average DPAB retention in timber [kg/m$^3$] | Average azol retention in timber [kg/m$^3$] |
|---|---|---|---|
| DPAB TGAI | | 4.50 | |
| azol | | | 0.10 |
| Product D | 1.16 | 1.15 | 0.01 |

DPAB = Crude betain with an Al content of 59%,
TGAl = Technical grade Al,
Al = the active ingredient,
DPAB TGAl = DPAB 59% Al - only 59% are active Al.

Table 15 shows that when using product D, a higher AI retention value of 1.16 against poria placenta can be achieved, again with using less DPAB (1.15 kg/m$^3$ instead of 4.50 kg/m$^3$) and azol (0.01 kg/m$^3$ instead of 0.10 kg/m$^3$).

TABLE 16

| Product | Average a.i. retention against *coniophora puteana* [kg/m$^3$] | Average DPAB retention in timber [kg/m$^3$] | Average azol retention in timber [kg/m$^3$] |
|---|---|---|---|
| DPAB TGAI | | 7.40 | |
| azol | | | 0.10 |
| Product D | 2.41 | 2.40 | 0.01 |

DPAB = Crude betain with an Al content of 59%,
TGAl = Technical grade Al,
Al = the active ingredient,
DPAB TGAl = DPAB 59% Al - only 59% are active Al.

Table 16 shows similar results, with an AI retention value of 2.41 when using smaller amounts of both cyclic compounds DPAB (2.40 kg/m$^3$ instead of 7.40 kg/m$^3$) and azol (0.01 kg/m$^3$ instead of 0.10 kg/m$^3$). These findings show that by again reducing the amounts of DPAB and azol by factors of 3 and 10 respectively; results are improved, once more noting that these results are achieved in the absence of copper.

From the above examples, objects of the invention have herein been fulfilled. A partial solution to at least one of the problems encountered in the state of the art in relation to a chromium-free wood preservative which can remain effective over a long period of time has been achieved. These results show that an increased performance can be achieved with a reduced amount of copper in the composition, thus indicating that the dispersion of copper particles within the composition and formulation is homogeneous, and therefore can remain effective at lower concentrations. These results show that by combining at least 2 heterocyclic B free organic compounds, both of which comprise at least one halogen atom, with a further cyclic organic compound comprising B, a synergy will be produced; and in doing so, will allow for a significant improvement in the AI retention in timber. When these compounds are further combined with copper, the results herein show that the same if not an improved performance against fungi (poria placenta/coniophora puteana) can be achieved compared to the comparative examples. Products A and B contain 66.52% (normalized) active copper compared with 93.99% (normalized) active copper used in the comparative example. This provides an additional advantage to the present invention in that less active organic ingredients are needed in order to achieve a quality timber protection. It is also clear that the invention has proven a reduced need for copper in a timber preservative. With a better performing composition, the longevity, durability and mechanical stability of timber and any construction using said timber will also be improved.

REFERENCE LIST

100 Vessel (100).
101 Sealed door (101) of vessel (100).
102 Interior view of vessel (100) and compartment (112).
103 Open door (103) of vessel (100) showing the interior (107) and layout of timbers (104) during treatment process.
104 Timbers (104) inserted into vessel (100).
105 Separators (105) used to create a horizontal gap between the stacked timbers (104).
106 Separators (106) used to create a vertical gap between the stacked timbers (104).
107 Interior of vessel (100).
108 Seal of cylindrical tubing (110) positioned within vessel (100).
109 Valve mechanism comprised in the cylindrical tubing (110) positioned within the vessel (100), which allows for transport of composition (113) from compartment (112) into the vessel.
110 Cylindrical tubing positioned within the vessel (100).
111 Opening at the end of cylindrical tubing (110) positioned within the vessel (100) to allow uptake of the composition (113) according to the invention from container (112).
112 Compartment comprising the composition (113).
113 The composition according to the invention.
200 Exterior wall (200) of a construction with exit onto a decked area (205).
201 Timber (201) preserved according to the invention, placed underneath and perpendicular to the upper layer of timbers (202) in order to give support to a deck (205).
202 Timbers (202) preserved according to the invention, connected at interfaces (203) in order to produce a deck (205).
203 Interfaces (203) of preserved timbers connected to form a deck (205).
204 Timbers (204) preserved according to invention, connected perpendicularly to horizontal timbers (202) of the deck (205) and vertical exit wall leading onto deck (200) in order to enclose the deck (205).
205 A deck (205) produced by assembling together timbers (201, 202, 204) preserved according to the invention.
206 Door of exterior wall of construction.
207 Window of exterior wall of construction.

The invention claimed is:
1. A composition comprising;
   i. a Cu-salt
   ii. at least one first cyclic organic compound comprising a B heteroatom in a cycle;
   iii. at least one further B free cyclic organic compound comprising a heteroatom selected from the group of O, N, S, or P, or a combination of at least two thereof in a cycle.
2. The composition according to claim 1, wherein the B heteroatom is negatively charged in the at least one first cyclic organic compound comprising a B heteroatom.
3. The composition according to claim 1, wherein the composition further comprises at least two different B free cyclic organic compounds.
4. The composition according to claim 3, wherein the at least two different B free cyclic organic compounds differ in at least one of the following structural terms:
   (a) the number of halogen atoms;
   (b) number of cycles;
   (c) number of heteroatoms other than halogens.
5. The composition according to claim 1, wherein the copper is present in the composition in a concentration in a range from 0.02-80 wt.-%.
6. The composition according to claim 1, wherein at least 60 wt.-% of the copper pre-sent in the composition has a particle size in the range from 1-1000 nm.
7. The composition according to claim 1, wherein the copper has a $d_{50}$ value in the range from 0.5-500 nm.
8. The composition according to claim 1, wherein the copper has a $d_{90}$ value in the range from 0.5-2000 nm.
9. The composition according to claim 1, wherein the copper has a $d_{10}$ value in the range from 0.08-500 nm.
10. The composition according to claim 1, wherein the Cu-salt is dispersed in a solvent wherein the solvent is a polar solvent, in order to obtain a liquid phase.
11. The composition according to any of claim 10, wherein the concentration of solvent lies in a range preferably from 1-60 wt.-% based on the total weight of the composition.
12. The composition according to claim 1, wherein the first cyclic organic compound is present in the composition in a range from 0.1-60 wt.-% based on the total weight of the composition.
13. The composition according to claim 1, wherein the at least one further cyclic compound is present in the composition in a range from 0.01-70 wt.-% based on the total weight of the composition.
14. The composition according to claim 1, wherein the first cyclic organic compound is a betain or its derivative or both.
15. The composition according to claim 1, wherein the further organic compound is a triazole or its derivative or both.
16. The composition according to claim 1, wherein the first cyclic organic compound has a moiety of the general formula (I):

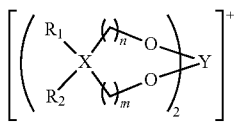

(I)

wherein in formula (I),

X is selected from elements P, N, or B;

Y is B;

R1, R2 are independently from each other a saturated linear hydrocarbon containing from 1-20 C atoms; and m and n are independently from each other any integer value in the range from 1-20.

17. The composition according to claim 1, wherein the further cyclic organic compound has a moiety of the general formula (II):

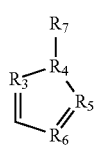

(II)

wherein in formula (II),

R3 is a heteroatom selected from elements C or N;

R4 is a non-C heteroatom selected from elements, N, O or S;

R5 is a heteroatom selected from elements C or N;

R6 is a heteroatom selected from elements, C, N, O or S; and

R7 is H, or comprises an organic moiety wherein the organic moiety can comprise at least one heteroatom selected from the group of C, H, O, N, halogen, or a combination of at least two thereof.

18. The composition according to claim 1, wherein the at least one further B free cyclic organic compound is selected from the group consisting of triadimefon, cyproconazol, tebuconazol, propriconazole or salts of each thereof.

19. The composition according to claim 3 wherein the at least two further B free cyclic organic compounds are tebuconazol and propriconazole or salts of each thereof.

20. A process for producing a composition, wherein the process comprises at least the following steps;
 i. providing a first cyclic organic compound comprising a B heteroatom;
 ii. providing at least one further B free cyclic organic compound comprising a heteroatom selected from the group of O, N, S, or P, or a combination of at least two thereof in a cycle;
 iii. providing a Cu-salt;
 iv. contacting the first cyclic organic compound comprising a B heteroatom with the at least one further B free cyclic organic compound in a solvent in order to obtain a solution; and
 v. contacting the solution of step (iv) with a Cu-salt in order to obtain the composition.

21. The process according to claim 20 wherein the Cu-salt is comprised in a liquid phase comprising a solvent.

22. The process for producing a composition according to claim 20, wherein the composition comprises at least two different further B free cyclic organic compounds.

23. The process for producing a composition according to claim 22, wherein in step iv. the contacting is performed at a temperature in the range from 30-80° C.

24. The process for producing a composition according to claim 20, wherein the first cyclic organic compound comprising a B heteroatom and the at least one further cyclic organic compound are contacted in a ratio of at least 1:25, wherein 1 is the concentration of the first cyclic organic compound and 25 is the concentration of the at least one further cyclic organic compound.

25. The process for producing a composition according to claim 20 wherein the Cu-salt liquid phase, is prepared at a temperature in the range from 5-60° C.

26. The process for producing a composition according to claim 20, wherein Cu-salt is ground.

27. The process for producing a composition according to claim 26, wherein the Cu-salt is ground until at least 50 wt.-% of the particles are less than 2000 nm in size.

28. The process for producing a composition according to claim 26, wherein the Cu-salt is ground until less than or equal to 30 wt.-% of the particles are smaller than 100 nm in size, based on the total weight of the composition.

29. The process for producing a composition according to claim 20, wherein the composition comprises:
 i. a Cu-salt
 ii. at least one first cyclic organic compound comprising a B heteroatom in a cycle;
 iii. at least one further B free cyclic organic compound comprising a heteroatom selected from the group of O, N, S, or P, or a combination of at least two thereof in a cycle.

30. A timber formulation comprising:
 a. a composition according to claim 1; and
 b. a timber;
 wherein the composition is present in the timber.

31. The timber formulation according to claim 30, wherein the timber comprises sap-wood in a range from 10-80 wt.-% of the timber.

32. A process for producing a timber formulation comprising the following process steps:
 a. providing a timber;
 b. applying an under-atmospheric pressure (vacuum);
 c. contacting the timber with a composition according to claim 1;
 d. applying an over-atmospheric pressure to the vessel in order to obtain the timber formulation.

33. The process according to claim 32, wherein the vacuum is in a range from 0.01 to 2.0 bar.

34. The process according to claim 32, wherein the water content of the timber is in a range from 5-50 wt.-% of the timber.

35. The process according to claim 32, wherein the over-atmospheric pressure is in the range from 1-15 bar.

36. The process according to claim 32, wherein the timber comprises at least 10 wt.-% sapwood.

37. The process according to claim 32, wherein the contacting in step c. is performed with a treating solution, wherein the treating solution comprises the composition being diluted by a solution solvent, wherein the concentration of the composition is in the range from 0.05-70 wt.-%, based on the treating solution.

38. A construction comprising a timber formulation according to claim 30 or obtainable by a process according to claim 32.

39. The construction according to claim 38, wherein the construction comprises an exterior surface which comprises the timber formulation, according to claim 30 or obtainable by a process according to claim 32.

40. The construction according to claim 39, wherein the exterior surface is of a sawed timber.

41. A use of a composition obtained by a process according to claim 20 to protect the exposed surface of a timber.

42. The use according to claim 41, wherein the timber is part of a wood comprising product.

43. The use according to claim 41, wherein the timber is comprised in an exterior surface.

44. A process for producing a timber formulation comprising the following process steps:
  a. providing a timber;
  b. applying an under-atmospheric pressure (vacuum);
  c. contacting the timber with a composition obtainable by the process according to claim 20;
  d. applying an over-atmospheric pressure to the vessel in order to obtain the timber formulation.

* * * * *